US009907729B2

(12) United States Patent
Nord et al.

(10) Patent No.: US 9,907,729 B2
(45) **Date of Patent: *Mar. 6, 2018**

(54) MEDICAL DEVICE CONNECTOR

(71) Applicant: Carmel Pharma AB, Göteborg (SE)

(72) Inventors: Lars Nord, Göteborg (SE); Alexander Cederschiöld, Gothenburg (SE)

(73) Assignee: Carmel Pharma AB, Göteborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,103

(22) Filed: Oct. 31, 2016

(65) Prior Publication Data

US 2017/0042768 A1 Feb. 16, 2017

Related U.S. Application Data

(63) Continuation of application No. 13/512,776, filed as application No. PCT/EP2009/065562 on Nov. 20, 2009, now Pat. No. 9,492,353.

(51) Int. Cl.
*A61M 5/32* (2006.01)
*A61J 1/20* (2006.01)

(52) U.S. Cl.
CPC ............. *A61J 1/2096* (2013.01); *A61J 1/201* (2015.05); *A61J 1/2055* (2015.05); *A61J 1/2065* (2015.05); *A61J 1/2089* (2013.01)

(58) Field of Classification Search
CPC ...... A61J 1/2006; A61J 1/2098; A61J 1/2089; A61J 1/2065; A61J 1/2055; A61J 1/201
See application file for complete search history.

(56) References Cited

U.S. PATENT DOCUMENTS

| | | | |
|---|---|---|---|
| 495,416 | A | 4/1893 | Jones |
| 4,564,054 | A | 1/1986 | Gustavsson |

(Continued)

FOREIGN PATENT DOCUMENTS

| | | |
|---|---|---|
| WO | 86/01712 | 3/1986 |
| WO | 2010/069359 | 6/2010 |

OTHER PUBLICATIONS

International Search Report in PCT/EP2009/065562, dated Aug. 16, 2010, 2 pgs.

*Primary Examiner* — Tatyana Zalukaeva
*Assistant Examiner* — Ariana Zimbouski
(74) *Attorney, Agent, or Firm* — Servilla Whitney LLC

(57) ABSTRACT

The present invention relates to a medical device connector for connecting a piercing device, with a vial comprising a base member. A plurality of grip members, each grip member comprising a distal end (D) and a proximal end (P) and each comprising a wedge portion adapted to temporarily or permanently lock the medical device connector to the vial. The base member further comprises a plurality of flanges, wherein the proximal ends (P) of the grip members are arranged to the flanges. The flanges extend substantially out from the periphery of the base member in a direction substantially perpendicular to the direction of the grip members, wherein the space formed between the flanges of the base member forms at least one grip portion. The present invention provides for a medical device connector which is easy and comfortable to use, which provide good stacking capabilities and which permits a user to readily acknowledge that the medical device connector is correctly assembled with the vial.

17 Claims, 6 Drawing Sheets

(56) References Cited

U.S. PATENT DOCUMENTS

| | | | |
|---|---|---|---|
| 4,759,756 | A | 7/1988 | Forman |
| 2002/0087144 | A1 | 7/2002 | Zinger |
| 2003/0153895 | A1 * | 8/2003 | Leinsing ............... A61J 1/2089 604/403 |

* cited by examiner

MEDICAL DEVICE CONNECTOR

CROSS-REFERENCE TO RELATED APPLICATIONS

This application is a continuation of U.S. patent application Ser. No. 13/512,776, filed May 30, 2012 and issued as U.S. Pat. No. 9,492,353 on Nov. 15, 2016, which is a national stage entry of PCT/EP2009/065562, filed on Nov. 20, 2009, which is incorporated herein by reference in its entirety.

TECHNICAL FIELD

The present invention relates to a medical device connector for connecting a piercing device with a vial. The medical device connector has grip members which are arranged on flanges enabling a snap on connection with the vial. The present invention enables a better and easier attachment of the medical device connector to a vial.

BACKGROUND OF THE INVENTION

Administration of hazardous medicaments such as cytotoxins and the like has long been a nuisance to the personnel which on a daily basis administrates the hazardous medicaments. During preparation of medicaments, administration or after treatment, nursing personnel is exposed to the risk of contamination from the hazardous medicaments. Such contamination may be in the form of liquid, aerosol or vapour medicaments, derived from spillage due to ill handling or just wrong handling of equipment or instruments. Leakage from technical equipment which has been used right is however also a problem, even if leakage occur in very small doses. Due to long exposure to hazardous medicaments nursing personnel can still become ill from very small quantities of hazardous medicaments. It is therefore important to minimize leakage and minimize the risk of leakage.

One specific hazardous step is when e.g. nursing personnel is transferring a medicament from one fluid container to another; such transfer usually involves the use of a piercing member such as a needle. To protect the nursing personal involved, piercing member protection devices are commonly used. Such devices are arranged to protect the user, not only from contamination but also from accidentally piercing themselves or any other third persons. One example of such a piercing member protection device, having a needle, is disclosed in U.S. Pat. No. 4,564,054 (Gustavsson).

Piercing devices, such as the ones described in the U.S. Pat. No. 4,564,054 (Gustavsson) generally require a mating connector or adaptor to enable assembly with a vial to prevent leakage. To enable a firm connection with a vial, medical device connectors, also referred to as medical device adaptors, for connecting piercing devices to vials have thus been developed.

Such medical device connectors are not seldom designed with a specific function in mind such as leakage security. This has generally led to more and more technically advanced connectors for connecting a piercing device to a vial in a leak safe manner.

SUMMARY OF THE INVENTION

It is the object of the present invention to provide for a simple and easy to use medical device connector for connecting a piercing device and a vial. According to the present invention this is achieved or at least partly achieved by a medical device connector for connecting a piercing device with a vial, the medical device connector comprises a base member with an extension in a plane. A plurality of grip members, each grip member comprising a distal end and a proximal end and each comprising a wedge portion adapted to temporarily or permanently keep the medical device connector connected to the vial. The base member further comprises at least one flange, wherein the proximal ends of the grip members are arranged on the at least one flange. The at least one flange extend substantially out from the periphery of the base member in a direction substantially perpendicular to the longitudinal direction of the grip members, wherein at least one space formed by the at least one flange of the base member forms at least one grip portion.

The present invention provides for a medical device connector which is easy and comfortable to use, which provides good stacking capabilities and which permits a user to readily acknowledge that the medical device connector is correctly assembled with the vial. The present invention enables a user to easily attach the medical device connector while at the same time provide a medical device connector with which a user easily can detect inconsistencies such as misalignment or inadequate attachment. The space is empty, i.e. devoid of any material.

It has been found that by having at least one space formed by the at least one flange, or preferably a plurality of spaces formed by a plurality of flanges, the medical device connector has a reduced tendency to roll. The reduced tendency to roll is advantageous during manufacturing as the medical device connector will be easier to handle or to transport on conveyor belts.

In an embodiment according to the present invention, to centre the piercing point to the vial, the base member comprises a through going aperture and a barrier member covering the aperture. This enables a double barrier member connection when used with a piercing device having a barrier member. Barrier members are generally made from rubber like material to seal around a needle of a piercing device when withdrawing medicals from the vial. The rubber like material can be silicone rubber or thermoplastic elastomers for example, although other materials are possible. Advantageously the through going aperture and a barrier member are arranged substantially at the centre of the base member, with respect to a centre axis.

Instead of having one flange which forms a space, i.e. the space being formed by a devoid of material, a plurality of flanges can be present. The pluralities of flanges extend substantially out from the periphery of the base member in a direction substantially perpendicular to the longitudinal direction of the grip members. A plurality of spaces formed between the flanges of the base member forms a plurality of grip portions.

The base member can be formed integrally or separately from the first and the second connection site. If the medical device connector is form molded, the first and the second connection site is generally integrally formed with the base member. The base member is generally a body around the barrier member, which can be said to carry or separate the first and the second connection site. The base member can be said to have an extension in a plane (PL). In an embodiment, the flanges extend substantially parallel with the plane of the base member. The plane of the base member is, in embodiments according to the present invention, perpendicular to the insertion direction of the piercing device, as outlined in the accompanying figures with the arrow X.

To attach and temporarily connect to a vial, the grip members can be arranged to extend substantially perpendicular to the plane of the base member. It has been found that the extension of the flanges, extending from the periphery of the base member, and extension of the grip members interact and can both improve the flexibility of the gripping function of the second connection site and the grip members.

Although it is advantageous to have four flanges and eight grip members, the base member of the medical device connector can be arranged with 3-8 flanges and 3-16 grip members. As an example, if there are 3 flanges there can be 6 grip members, two on each flange. The base member can thus comprise twice as many grip members as flanges. However some embodiments can have an equal number of flanges and grip members. As an option combinations of flanges having two grip members and flanges having one grip member are possible.

To provide a better rigidity, in an embodiment according to the present invention, bridge sections can be arranged between at least parts of the grip members or optionally between all of the grip members. In the embodiments in which the flanges of the base member comprise two grip members, the bridge sections preferably extend between the grip members of separate flanges. Hence, in that embodiment, there are no bridge sections between grip members which extend from the same flange. A bridge section is generally formed from the same material as the grip member, the flange and the base member, and optionally as the first and the second connection site, as it is beneficial to form mold the whole piece. The bridge sections provide for improved rigidity, giving structural integrity to the second connection site permitting less material to be used during the manufacturing step. A good rigidity is achieved when the bridge sections are arranged substantially between the distal ends of the grip members.

In embodiments where there are no bridge sections, wedge portions can be arranged at the distal ends of the grip members to provide for a snap on connection to the vial, however, in embodiments where bridge sections are used, each the bridge section comprises a wedge portion. The wedge portion is adapted to lock, temporarily or permanently, the medical device connector to the vial. As the wedge portion of the grip members is mounted onto the vial, the grip members are deformed and pressed aside. When the wedge portion has passed the neck of the vial, the grip members tend to return to their original position, hooking the neck of the vial by means of the wedge portion which also forms a hook surface or hook portion.

As mentioned, the grip members deform when attaching or detaching the medical device connector from the vial to be substantially returned to their original position, thereby holding the medical device connector in position. In an embodiment according to the present invention, the flanges of the base member can also be flexible, permitting temporary deformation during assembly with the vial. Hence both the flanges and the grip members can be flexible and thus both deform, permitting temporary deformation during assembly with the vial. Optionally, the flange or the grip members are flexible.

The medical device connector has been found to be stackable. The stackable function of the medical device connector enables larger quantities of the medical device connector to be packaged in relatively small packages. The present invention thus includes a first and a second medical device connector arranged to form a stack of medical device connectors. At least parts of the grip members of the first medical device connector are arranged to rest on at least parts of the flanges of the base member of the second medical device connector, optionally at least parts of the distal ends of the grip members of the first medical device connector are arranged to rest on at least parts of the flanges of the base member of the second medical device connector. In an embodiment according to the present invention, the bridge sections of the first medical device connector are arranged at least partly, or optionally fully, between the grip members of the second medical device connector.

BRIEF DESCRIPTION OF THE DRAWINGS

The present invention will de described in greater detail with reference to the accompanying figures in which.

DEFINITION

By the term “medical device” is meant a device used in hospital environments, nursing environments or care taking environments usually by qualified personnel such as doctors, nurses or the like. Such environments generally have high requirements regarding hygiene, personal care, and a strive towards low risk for contaminations. Typical medical devices are needles, syringes, piercing member protection devices, vials, infusion bags, infusion sets, administration systems, adapters, tubes, medical device connectors for connecting or adapting different medical devices to each other, or the like.

DETAILED DESCRIPTION OF PREFERRED EMBODIMENTS

Figure 1:
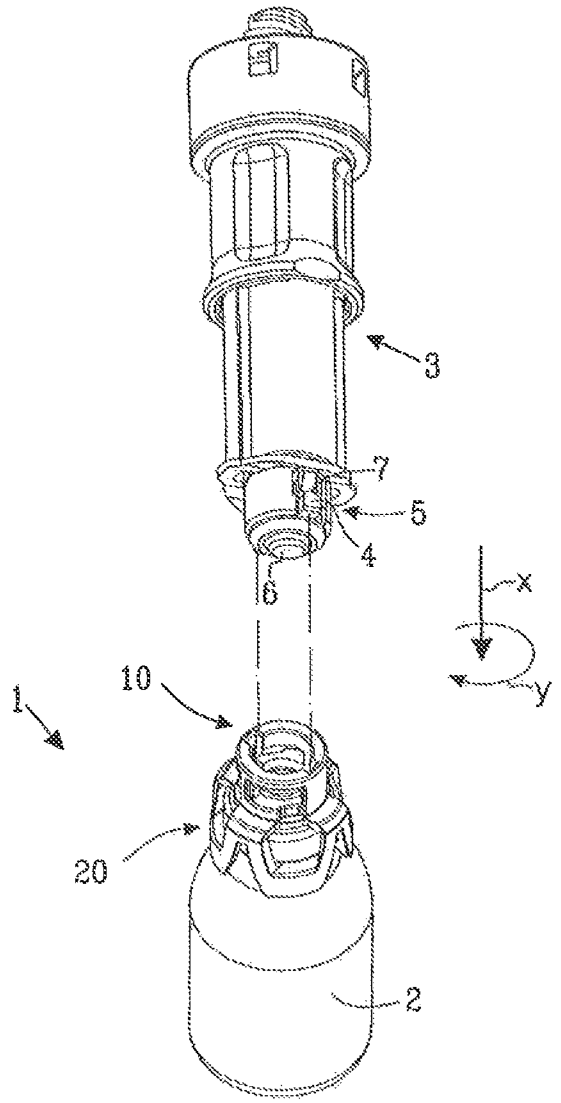
FIG. 1 shows a piercing device in the form of a piercing device protection device with a needle, a medical device connector and a vial; the medical device connector being connected to the vial.

FIG. 1 shows a medical device connector 1 for connecting two medical devices. The medical devices can be a vial 2 and a piercing device 3. The piercing device 3 can be a piercing device having a telescopically movably piercing member protection function. The medical device connector 1 comprises a first connection site 10 adapted to receive and establish a connection with the piercing device 3 and a second connection site 20 adapted to establish a connection with the vial 2. The second connection site 20 operates by being fitted onto the neck of the vial 2 with a snap on function.

Figure 2A:
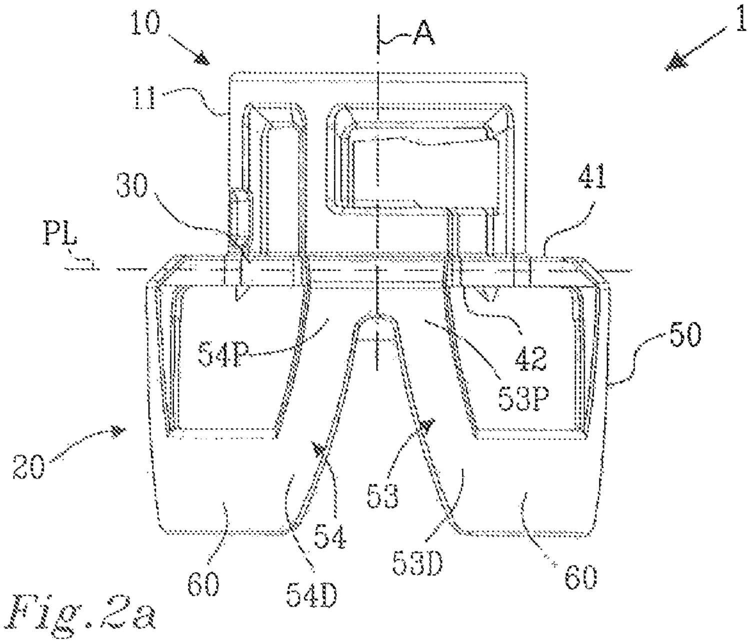
FIGS. 2*a*-2*c* show the medical device connector from FIG. 1 shown in different views.
Figure 2B:
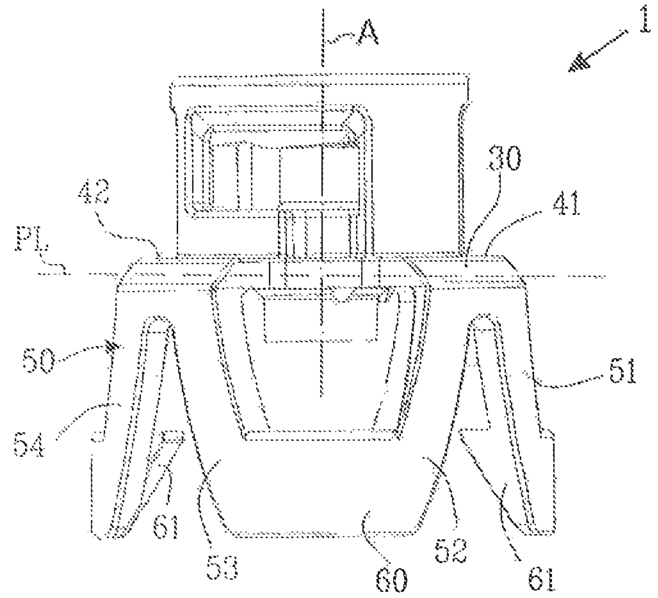
Figure 2C:
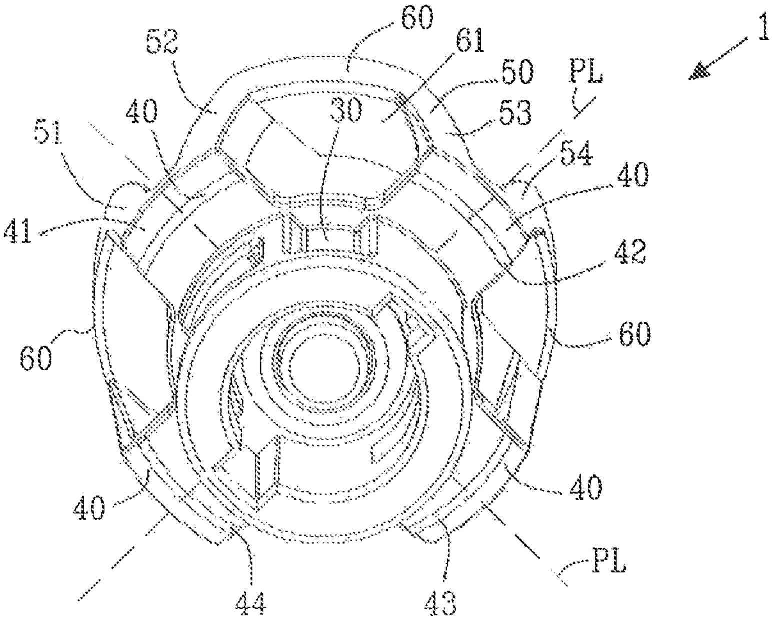

FIGS. 2*a*-2*c* show the medical device connector 1 in different views, the same feature is indicated with the same reference numeral. FIGS. 2*a*-2*c* shows the first and the second connection site 10, 20 arranged on a base member 30. The medical device connector 1 has a centre axis A. The base member 30 separates the first and the second sites 10, 20 from each other but is formed integrally with the first and the second connection sites. The base member 30 has an extension in the plane PL, as indicated in FIGS. 2*a*-2*c*.

A plurality of flanges 40 extends from the periphery of the base member 30. The embodiment shown in FIGS. 2*a*-2*d* has four symmetrically positioned flanges 40; a first, a second, a third and a forth flange 41, 42, 43, 44, extending parallel with the plane PL out from the periphery of the base member 30. The flanges 40 are formed integrally with the base member 30 but can be formed separately and connected thereto. A plurality of grip members 50 are arranged on the base member 30 via the flanges 40 and substantially perpendicular to the flanges 40. The flanges 40 extend in a direction substantially perpendicular to the longitudinal direction of the grip members 50. In the shown embodiment, each flange member 41, 42, 43, 44 comprises two grip members 51, 52, 53, 54 (not all grip members are shown). The grip members 51, 52, 53, 54 are flexible and will deform somewhat as the they are connected to the vial 2, to thereafter return substantially to their original position after passing a flange on the vial 2, whereafter the grip members connect the medical device connector 1 to the vial 2 in a known snap-on manner.

FIG. 2*a* shows a view towards the second flange 42 and the two grip members 53, 54 of the second flange 42. Each grip member 50 of the medical device connector 1 comprises a proximal end P and a distal end D, in FIG. 2*a* this is illustrated by the grip member 53 having a proximal end $\mathbf{53}_P$ and a distal end $\mathbf{53}_D$. The proximal ends are connected to the base member 30.

Between each adjacent grip member 52, 53 of separate flanges 41, 42, a bridge section 60 is provided, thus four bridge sections 60 are provided. As is noticed, the bridge sections 60 extend from the distal ends D of the grip members and thereby connect the distal ends $\mathbf{52}_D$, $\mathbf{53}_D$ of the grip members 52, 53 of separate flanges 41, 42. Each bridge section 60 comprises a wedge portion 61 enabling a snap on function to the vial 1 shown in FIG. 1.

Figure 2D:
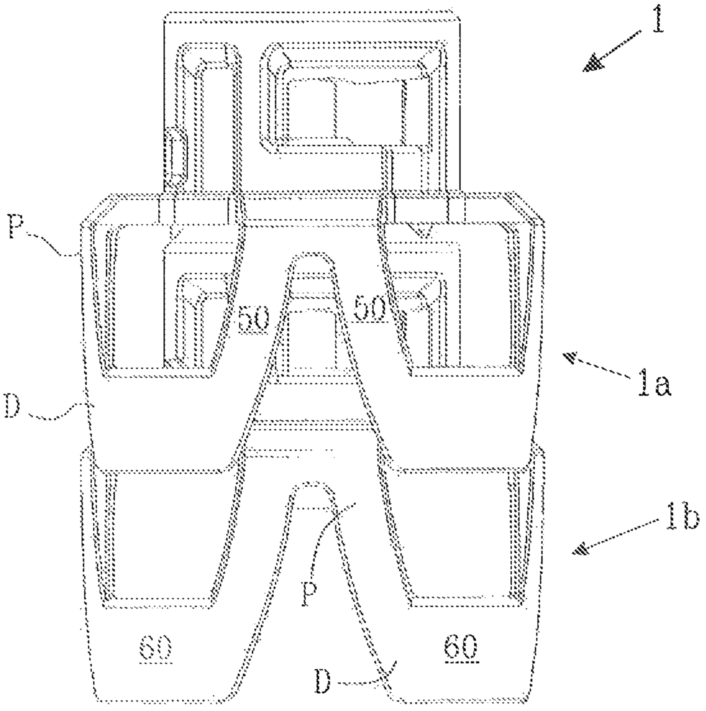
FIG. 2*d* shows two medical device connectors, as shown in FIG. 1, piled in a stack of medical device connectors.

The distance between the proximal ends P is smaller than the distance between the distal ends of the grip members. This provides for grip members having a somewhat tilted appearance and extending in a non parallel direction with respect to the centre axis A. This enables a plurality of medical device connectors 1*a*, 1*b* to be stacked in a relatively compact manner, as shown in FIG. 2*d*. In an embodiment of the present invention, the distance between the distal ends D of grip members 50 arranged on the same flange 40, is larger than the width of the flanges 40.

Figure 3:
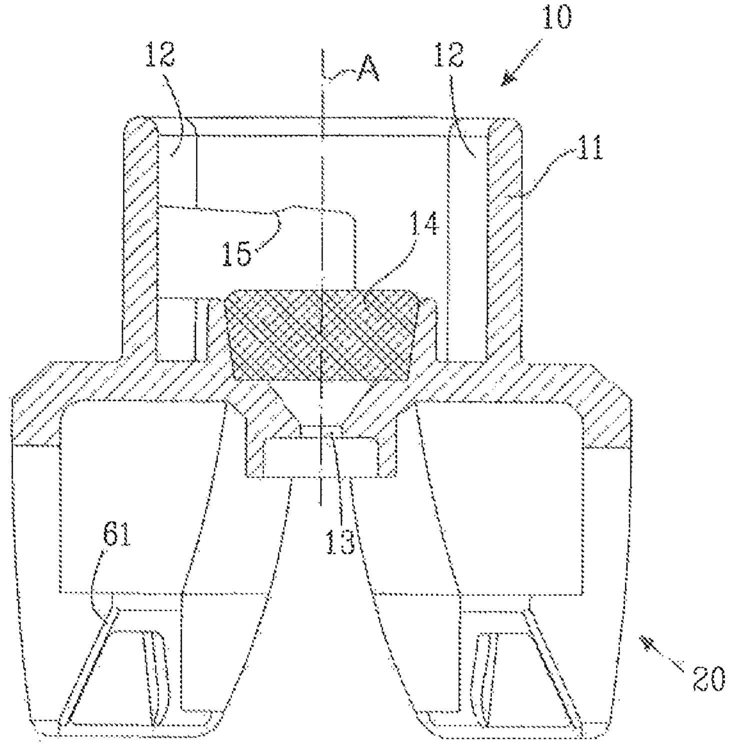
FIG. 3 shows a cross section of the medical device connector shown in FIG. 1.

FIG. 3 shows a cross section of the medical device connector 1, shown in FIGS. 1, and 2*a*-2*d*. The first connection site 10 comprises a neck element 11 having two guiding tracks 12 (e.g. shown in FIG. 2*c*) for receiving lock protrusions 4 of the piercing device 3, shown in FIG. 1. Each guiding track 12 comprises a locking edge 15. The lock protrusions 4 of the piercing device 3 cooperate with the locking edge 15 to connect the piercing device 3.

Intersecting with the centre axis A is a through going aperture 13 arranged to permit a needle of the piercing device 3 to extend therethrough after assembly and during use. A barrier member 14 from e.g. a silicone rubber material is arranged to seal around such needle during use. The barrier member 14 covers the through going aperture.

Figure 4:
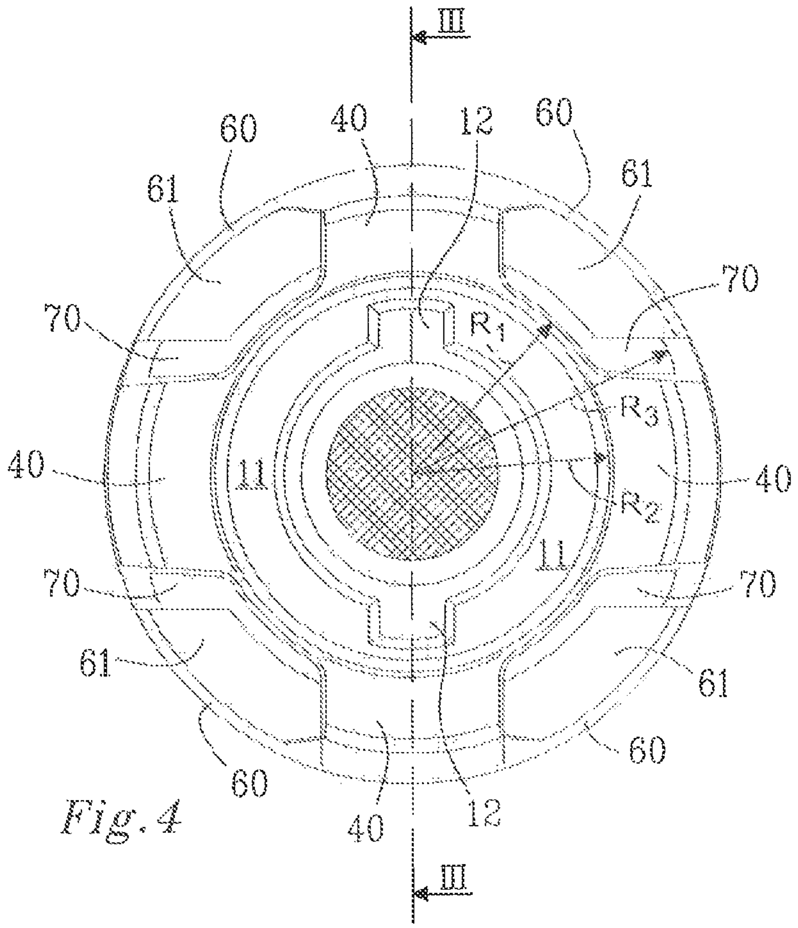
FIG. 4 shows the medical device connector as shown in FIG. 1 from above, along the centre axis A.

FIG. 4 shows the medical device connector 1 with a view along the centre axis A and from above. As is noted, the base member 30 has a radius $R_1$, which substantially corresponds to a radius $R_2$ of the neck element 11 of the first connection site 10. Each flange 40 further extends to a radius $R_3$ which is larger than the radius $R_1$ of the base member 30. This enables the wedge portions 61 to be seen between the flanges 40. The radius R3 corresponds substantially to the largest radius of the vial neck at which the grip members 50 are intended to be held. This further enables the vial to be readily seen between the flanges 40 as is illustrated in FIG. 1. The grip portions formed between the flanges 40 thus have a dual functionality of operating as a window for confirming proper alignment and adequate attachment of the medical device connector 1 to the vial 3.

Furthermore, it is possible to construct a medical device connector 1 which has through going openings 70 when seen along the centre axis A. It has been found that these through going openings 70, one opening for each bridge section 60 and wedge portion 61, enable the medical device connector 1 to be manufactured very easily. The medical device connector 1 can for example be form molded, during such form molding, the insertion and retraction direction of the form molding tools have an impact on the manufacturing rate of the manufacturing process.

Figure 5:
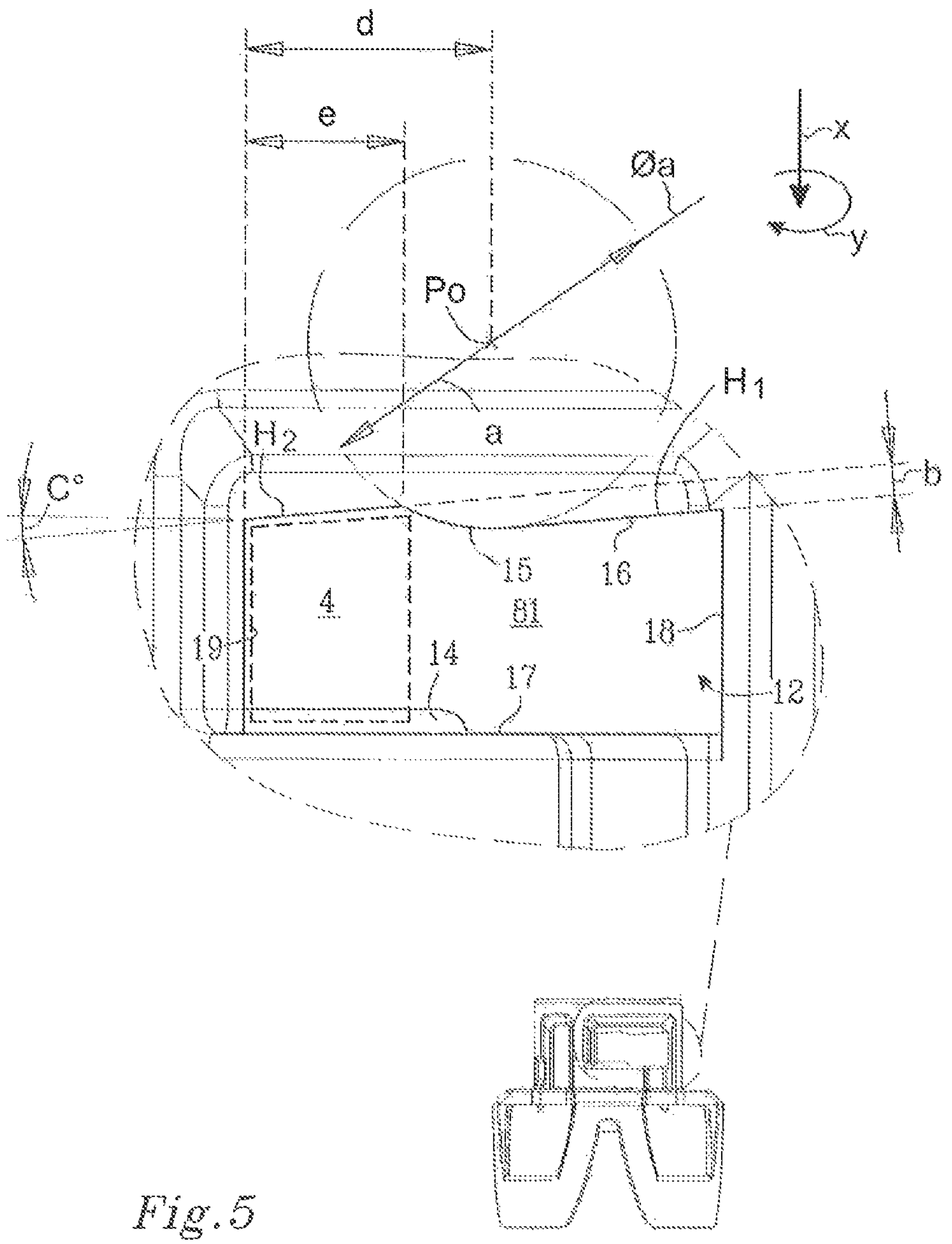
FIG. 5 shows an enlargement of the neck element of the first connection site of the medical device connector.

FIG. 5 shows an enlargement of parts of the neck element 11 and one of the guiding tracks 12 of the first connection site 10 of the medical device connector 1, as seen in FIGS. 1-4. The guiding track 12 comprises the locking edge 15, which the lock protrusions 4 of the piercing device 3 is intended to cooperate with during assembly, as illustrated in FIG. 1. The tip 5 of the piercing device 3, with its barrier member 6 and lock protrusions 4, as shown in FIG. 1, is inserted into the neck element 11 of the first connection site 10. The lock protrusions 4 of the piercing device 3 slide in the guiding tracks 12 in a cooperative manner.

The arrows X, Y, shown in FIGS. 1 and 5, show how the piercing device 3 is moved during insertion and in which order; X before Y. Disengagement in executed in the opposite order and direction; Y before X. First, with a vertical motion illustrated by arrow X, the tip 4 of the piercing device 3 is inserted so that the barrier member 6 of the piercing device 3 is positioned directly adjacent the barrier member 14 of the medical device connector 1, shown in FIG. 3. As the barrier members 6, 14 are compressed by the vertical movement, the lock protrusions 4 of the piercing device 3 are aligned with the horizontal part of the guiding tracks 12 and the piercing device 3 can be turned clockwise, as indicated by the arrow Y. During the clockwise turning, which in an embodiment of course can be counter clockwise, an upper surface 7 of the lock protrusion 4 slides against an upper surface 16 of the guiding track 12. As is noticed, the neck element 11 comprises two guiding tracks 12 and the piercing device 3 comprises two lock protrusions 4, although each feature might be described in the singular. In FIG. 5, parts of the lock protrusion 4 of the piercing device 3 are indicated with a dotted line and shown in the locked position.

As is noticed in FIG. 5, the locking edge 15 extends in a smooth curvature between a first and a second level, illustrated with the distance b in FIG. 5. The locking edge 15 extends in a smooth curvature, the curvature of which is a function of a radius, indicated by the diameter Øa, the radius a, being half of the diameter Øa. The radius a can be 1-10 mm, preferably 2-8 mm even more preferably 3-5 mm. In the embodiment shown in FIG. 5, the radius a is about 3 mm. The locking edge thus enables a good connection between the piercing device 3 and the medical device connector 1 which is especially easy to unlock, but also easy to lock. The locked position is indicated in FIG. 5 with the doted lines of the lock protrusion 4. In an embodiment, the locking edge 15 extends as a smooth curvature, the curvature which is a function of at least two radii, preferably two radii, different or the same, but with a different point of origin.

The upper surface 16 of the guiding tracks 12 is further arranged with an angle c, as indicated in FIG. 5 with respect to a lower surface 17 of the guiding tracks 12. The lower surface 17 of the guiding tracks 12 can be considered to be horizontal, or parallel with a still water line. The angle c is advantageously 0-15°, preferably 2-10°, even more preferably 5-7°. In the shown embodiment the angle c is 5°. The angled surface enables the piercing device 3 to be compressed towards the medical device connector 1 during assembly and the clockwise turning of the piercing device 3, as indicated by arrow Y in FIG. 5.

What is claimed is:

1. A medical device connector comprising;

a base member having a through going aperture;

a first connection site and a second connection site connected by the base member, wherein the first connection site comprises a neck element having two guiding tracks, wherein the two guiding tracks comprising an upper surface and a lower surface, the upper surface of the two guiding tracks being arranged with an angle with respect to the lower surface of the two guiding tracks;

a plurality of grip members, each grip member comprising a distal end and a proximal end and each grip member comprising a wedge portion adapted to temporarily or permanently keep the medical device connector to a vial;

wherein the base member comprises a plurality of flanges, wherein the proximal ends of the grip members are arranged on the plurality of flanges, the plurality of flanges extend out from a periphery of the base member in a direction perpendicular to a longitudinal direction of the grip members, wherein a plurality of spaces formed between the plurality of flanges of the base member form a plurality of grip portions, each flange of the base member comprises two grip members and bridge sections extend between the grip members of separate flanges.

2. The medical device connector of claim 1, wherein the upper surface of the two guiding tracks is arranged with an angle between 0-15° with respect to the lower surface of the two guiding tracks.

3. The medical device connector of claim 1, wherein the second connection site comprises the grip members.

4. The medical device connector of claim 1, wherein the two guiding tracks of the neck element are adapted to receive a lock protrusion of a medical device.

5. The medical device connector of claim 4, wherein the medical device is a piercing device.

6. The medical device connector of claim 1, a locking edge extending in a smooth curvature between a first level and a second level.

7. The medical device connector of claim 1, wherein the base member comprises a barrier member covering the through going aperture.

8. The medical device connector of claim 7, wherein the through going aperture and the barrier member are arranged at a centre of the base member.

9. The medical device connector of claim 1, wherein the plurality of flanges extends parallel with a plane of the base member.

10. The medical device connector of claim 1, wherein the base member comprises 2-20 flanges and 2-40 grip members.

11. The medical device connector of claim 1, wherein the base member comprises twice as many grip members as flanges.

12. The medical device connector of claim 1, wherein the bridge sections are arranged between the distal ends of the grip members.

13. The medical device connector of claim 1, wherein each bridge section comprises at least parts of the wedge portion adapted to lock the medical device connector to the vial.

14. The medical device connector of claim 1, wherein the flanges of the base member are arranged to be flexible, permitting temporary deformation during assembly with the vial.

15. The medical device connector of claim 1, wherein the grip members are arranged to be flexible, permitting temporary deformation during assembly with the vial.

16. The medical device connector of claim 1, wherein a distance between the proximal ends of the grip members is smaller than a distance between the distal ends of the grip members.

17. The medical device connector of claim 1, wherein the plurality of flanges have a radius larger than a radius of the base member.

* * * * *